US012569273B2

(12) United States Patent
Tada et al.

(10) Patent No.: US 12,569,273 B2
(45) Date of Patent: Mar. 10, 2026

(54) MEDICAL DEVICE

(71) Applicant: TERUMO KABUSHIKI KAISHA, Tokyo (JP)

(72) Inventors: Yuichi Tada, Santa Clara, CA (US); Yoichiro Kuwano, Machida City (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 128 days.

(21) Appl. No.: 18/474,458

(22) Filed: Sep. 26, 2023

(65) Prior Publication Data

US 2024/0108378 A1 Apr. 4, 2024

(30) Foreign Application Priority Data

Sep. 29, 2022 (JP) .................................. 2022-156351

(51) Int. Cl.
*A61B 17/3207* (2006.01)
*A61B 17/32* (2006.01)

(52) U.S. Cl.
CPC ................. *A61B 17/320758* (2013.01); *A61B 2017/320052* (2013.01); *A61B 2017/320716* (2013.01); *A61B 2217/007* (2013.01)

(58) Field of Classification Search
CPC .... A61B 17/320758; A61B 17/320725; A61B 17/32075; A61B 17/320783; A61B 17/32002
See application file for complete search history.

(56) References Cited

U.S. PATENT DOCUMENTS

| | | | | |
|---|---|---|---|---|
| 4,819,634 A | * | 4/1989 | Shiber | A61B 18/245 604/95.01 |
| 9,717,520 B2 | | 8/2017 | Zeroni et al. | |
| 2007/0250096 A1 | * | 10/2007 | Yamane | A61B 17/22 606/159 |
| 2007/0255252 A1 | | 11/2007 | Mehta | |
| 2019/0038300 A1 | * | 2/2019 | Savastano | A61M 25/09 |
| 2022/0346820 A1 | | 11/2022 | Tada | |

FOREIGN PATENT DOCUMENTS

WO 2021/199212 A1 10/2021

OTHER PUBLICATIONS

Notice of Reasons for Refusal issued on Oct. 14, 2025, by the Japanese Patent Office in Japanese Patent Application No. 2022-156351 and an English translation of the Action. (11 pages).

* cited by examiner

*Primary Examiner* — Tuan V Nguyen
(74) *Attorney, Agent, or Firm* — BUCHANAN INGERSOLL & ROONEY PC

(57) ABSTRACT

A medical device includes: an elongated shaft portion that includes a drive shaft which is rotatable and a fluid lumen; and a cutter that cuts an object, the cutter being fixed to a distal end of the drive shaft and including a lumen communicating with the fluid lumen and a distal end opening communicating with the lumen, wherein the cutter has at least one guide portion that is a groove and/or a slit on an outer peripheral surface, and the guide portion extends in a direction opposite to a rotation direction in a distal direction.

18 Claims, 9 Drawing Sheets

*FIG. 1*

MEDICAL DEVICE

CROSS-REFERENCES TO RELATED APPLICATIONS

This application claims priority to Japanese Patent Application No. 2022-156351 filed on Sep. 29, 2022, the entire content of which is incorporated herein by reference.

TECHNOLOGICAL FIELD

The present invention generally relates to a medical device for removing an object in a body lumen.

BACKGROUND DISCUSSION

Examples of a method for treating a stenosed part due to plaque, thrombus, or the like in a blood vessel include a method for expanding the blood vessel with a balloon and a method for placing a meshed or coiled stent in the blood vessel as a support of the blood vessel. However, with these methods, it is difficult to treat a stenosed part hardened due to calcification or a stenosed part generated in a bifurcation of a blood vessel. As a method with which it is possible to treat the stenosed part even in such a case, there is a method for cutting and removing an object causing stenosis such as plaque or thrombus.

For example, U.S. Pat. No. 9,717,520 describes a device that rotates a cutter disposed at a distal end to cut an object in a blood vessel and suctions generated cut debris through a suction port.

SUMMARY

In a case where an acting portion, where the cut debris is generated, and the suction port are not close to each other, or in a case where the suction port is on the upstream side of the blood flow with respect to the acting portion, the device may not be able to collect the cut debris.

The medical device disclosed here can effectively collect cut debris.

The medical device is able to effectively collect cut debris by the aspect described in (1) below.

(1) According to one aspect, a medical device includes: an elongated shaft portion that includes a drive shaft which is rotatable and a fluid lumen; and a cutter that cuts an object, the cutter being fixed to a distal end of the drive shaft and including a lumen communicating with the fluid lumen and a distal end opening communicating with the lumen, wherein the cutter has a guide portion that is a groove and/or a slit on an outer peripheral surface, and the guide portion extends in a direction opposite to a rotation direction in a distal direction.

In the medical device configured as described above, when the cutter rotates, the guide portion applies a force to the distal side to a contacting object. Therefore, the medical device can guide cut debris generated by cutting by the cutter to the distal side where the distal end opening is formed, and can effectively collect the cut debris into the lumen communicating with the fluid lumen.

(2) In the medical device described in (1), at least a part of the guide portion is a slit penetrating from the outer peripheral surface to an inner peripheral surface of the cutter. With this configuration, the medical device can directly guide and collect the cut debris to the lumen of the cutter, in addition to guiding the cut debris to the distal side by the guide portion.

(3) In the medical device described in (1) or (2), at least a part of the guide portion is a groove formed in the outer peripheral surface of the cutter. With this configuration, the medical device can limit the depth of the guide portion, thereby being capable of cutting a cutting target while suppressing an occurrence of blood vessel perforation and the like by preventing damage of a contacting living tissue. In addition, the medical device can limit a collection path for collecting the cut debris into the lumen of the cutter communicating with the fluid lumen to the distal end opening. Therefore, the medical device can suppress excessive discharge of blood by the fluid lumen.

(4) In the medical device described in (3), a depth of the groove of the guide portion is deeper on a distal side than on a proximal side of the cutter. With this configuration, the medical device can increase a flow path on the side in the distal direction, which is a direction in which the cut debris is conveyed, in the guide portion, thereby being capable of effectively conveying the cut debris to the distal side.

(5) In the medical device described in any one of (1) to (4), a width of the guide portion that is a length in a direction perpendicular to an extending direction of the guide portion on the outer peripheral surface of the cutter is greater on a distal side than on a proximal side of the cutter. With this configuration, the medical device can increase a flow path on the side in the distal direction, which is a direction in which the cut debris is conveyed, in the guide portion, thereby being capable of effectively conveying the cut debris to the distal side.

(6) In the medical device described in any one of (1) to (5), the guide portion includes a cutting element that cuts an object. With this configuration, the medical device can cut the cutting target by the guide portion formed on the outer peripheral surface of the cutter, and thus, can directly guide the cut debris generated in the guide portion to the distal side in the guide portion and effectively collect the cut debris into the lumen, while effectively cutting the cutting target.

(7) In the medical device described in (6), the cutting element is disposed on the guide portion at a position different from a position of a large-diameter portion having a maximum outer diameter of the cutter. With this configuration, the medical device can effectively cut the cutting target while suppressing the occurrence of blood vessel perforation and the like by preventing damage of a contacting living tissue.

(8) In the medical device described in (6) or (7), the cutting element is disposed radially inside a section having a maximum outer diameter in a cross section orthogonal to a rotation axis. With this configuration, the medical device can effectively cut the cutting target while suppressing the occurrence of blood vessel perforation and the like by preventing damage of a contacting living tissue.

(9) In the medical device described in any one of (1) to (8), the cutter includes a plurality of blades arranged at a distal end of the cutter so as to surround the distal end opening, and the guide portion communicates with the distal end opening between two of the blades that are adjacent to each other. With this configuration, the medical device enables the cut debris guided to the distal side by the guide portion to effectively reach the distal end opening through a gap that is easily ensured between the two blades.

(10) In the medical device described in any one of (1) to (9), the guide portion may have a guide surface. With this configuration, the medical device can effectively apply a force to the cut debris or a liquid containing the cut debris by the guide surface to thereby effectively guide the cut debris in the distal direction.

Another aspect of the disclosure involves a medical device positionable inside a lumen in a living body and operable to cut an object in the lumen. The medical device comprises an elongated drive shaft having a proximal end and an open distal end, with the drive shaft including a fluid lumen that fluidly communicates with the open distal end of the drive shaft and that extends from the open distal end of the drive shaft toward the proximal end of the drive shaft, and with the drive shaft being a rotatable drive shaft that is rotatably driven in a rotational direction during operation of the medical device. A cutter is fixed to the distal end of the drive shaft so that the cutter rotates with the drive shaft about a rotational axis of the cutter. The cutter has a distal portion configured to cut the object, and the cutter includes a lumen that is in fluid communication with the fluid lumen in the drive shaft, with the lumen in the cutter communicating with outside the cutter. The cutter includes a groove and/or a slit that extends radially from the outer peripheral surface of the cutter toward the lumen in the cutter, and the cutter includes a cutting element that extends along at least a portion of the groove and/or slit to cut the object when the cutter is rotated, with the cutting element being located proximal of the distal portion of the cutter that is configured to cut the object.

Another aspect of the disclosure involves a method comprising positioning a cutter in a lumen in a living body, wherein the cutter is connected to a drive shaft and includes a lumen that is in fluid communication with an open distal end of the cutter. The lumen in the cutter extends in a proximal direction from the open distal end of the cutter toward the drive shaft, and the cutter includes an outer peripheral surface provided with a groove and/or a slit extending in a first rotational direction in a distal direction. The method also comprises moving the cutter to an object in the lumen in the living body, and rotating the cutter in a second rotational direction opposite the first rotational direction while the cutter is positioned adjacent the object so that the cutter cuts the object to produce debris.

BRIEF DESCRIPTION OF THE DRAWINGS

FIG. 1 is a front view of an entire medical device according to one embodiment disclosed here;

FIGS. 6A and 6B are diagrams illustrating the cutter, in which FIG. 6A is a cross-sectional view taken along the section line 6A-6A in FIG. 5, and FIG. 6B is a cross-sectional view taken along the section line 6B-6B in FIG. 5.

FIGS. 8A and 8B are cross-sectional views illustrating modifications of the cutter, in which FIG. 8A illustrates a first modification, and FIG. 8B illustrates a second modification.

FIGS. 9A to 9C are front views illustrating modifications of the cutter, in which FIG. 9A illustrates a third modification, FIG. 9B illustrates a fourth modification, and FIG. 9C illustrates a fifth modification.

DETAILED DESCRIPTION

Figure 2:
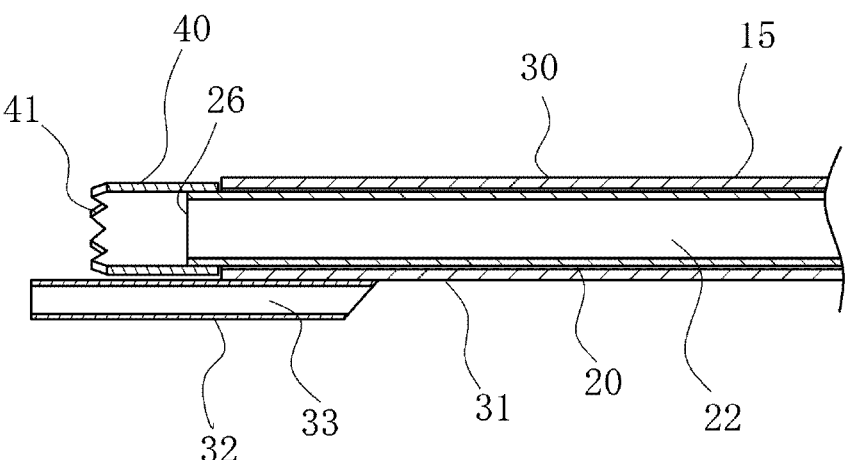
FIG. 2 is an enlarged cross-sectional view of an area near a distal end part of the medical device.

An embodiment of the medical device disclosed here will be described below with reference to the drawings. Dimensional ratios in the drawings may be exaggerated and may be different from actual ratios for convenience of description. In addition, in the present specification, a side on which a medical device 10 is inserted into a body lumen will be referred to as a "distal end" or a "distal side", and a side operated by an operator will be referred to as a "proximal end" or a "proximal side".

The medical device 10 according to the present embodiment is inserted into a blood vessel in acute lower limb ischemia or deep-vein thrombosis, and used for a treatment including destroying and removing an object in the blood vessel such as a thrombus, a plaque, an atheroma, and a calcified lesion. The object to be removed is not necessarily limited to the thrombus, the plaque, the atheroma, and the calcified lesion, and may be any object that can be present in the body lumen.

Figure 1:
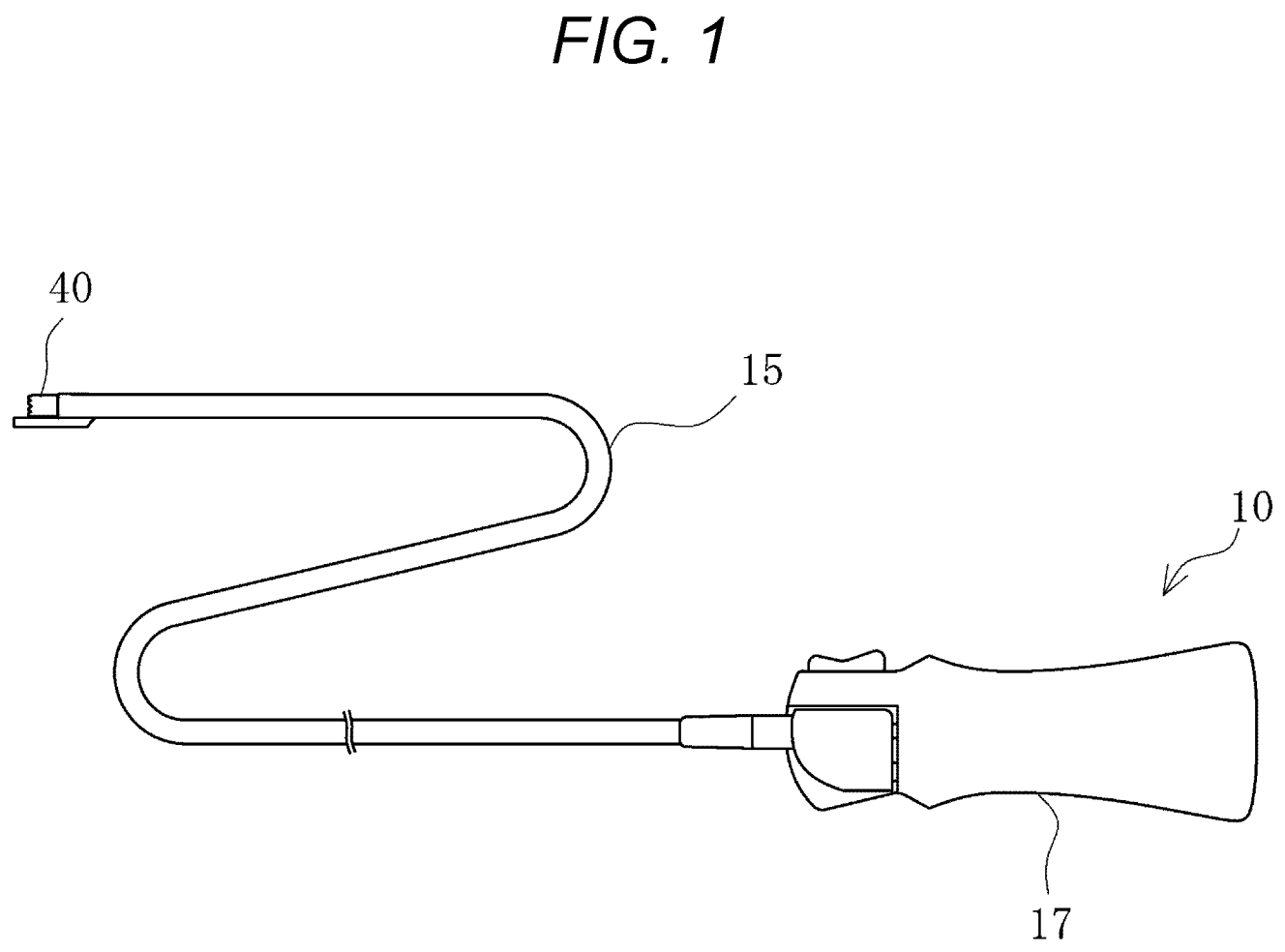

As illustrated in FIGS. 1 and 2, the medical device 10 includes a shaft portion 15 having a long (elongated) drive shaft 20 that is rotationally driven and an outer tube 30 that accommodates the drive shaft 20. A handle 17 is provided at the proximal end part of the shaft portion 15. A cutter 40 for cutting an object such as thrombus is provided at the distal end part of the drive shaft 20.

The drive shaft 20 transmits a rotational force to the cutter 40. The drive shaft 20 is specified to rotate in one direction when the cutter 40 cuts the object. The drive shaft 20 is provided with a fluid lumen 22 for conveying a cut object to the proximal side. The drive shaft 20 penetrates or passes through the outer tube 30 and has the cutter 40 fixed to a distal end part of the drive saft 20. The drive shaft 20 has, at the distal end, an inlet port 26 through which cut debris S (cut thrombus or the like) that is an object to be sucked enters.

The drive shaft 20 is flexible and has a property of transmitting rotational power applied from the proximal side to the distal side. The drive shaft 20 may be constituted by a single member, or may be constituted by a plurality of members. The drive shaft 20 may be formed with a helical slit or groove by laser processing or the like in order to adjust rigidity depending on sections. The distal end part and the proximal end part of the drive shaft 20 may be formed of different members.

Examples of a material that can be preferably used for the drive shaft 20 include stainless steel, a shape memory alloy such as a nickel-titanium alloy, an alloy (silver brazing filler metals component) made of silver, copper, zinc, or the like, an alloy (solder component) made of gold, tin, or the like, hard metal such as tungsten carbide, a polyolefin such as polyethylene or polypropylene, polyamide, polyester such as polyethylene terephthalate, a fluorine-based polymer such as ethylene tetrafluoroethylene copolymer (ETFE), polyetheretherketone (PEEK), and polyimide. In addition, the drive shaft 20 may include or be made of a plurality of materials, and may have a reinforcing member such as a wire embedded therein.

The outer tube 30 includes an outer tubular body 31 that houses the drive shaft 20 in a rotatable manner, and a distal tube 32 fixed to a side face of the outer tubular body 31 at the distal end part of the outer tubular body 31.

The distal end part of the outer tubular body 31 is located on the proximal side of the cutter 40. The cutter 40 can be directed to the object to be removed by rotating the outer tubular body 31. In addition, the outer tubular body 31 may have a bending portion that bends at a predetermined angle at the distal end part. Due to the bending portion, the cutter 40 can be easily brought into contact with the object to be removed by rotating the outer tubular body 31.

The distal tube 32 is fixed to the outer peripheral surface of the outer tubular body 31 at the distal end part. The distal tube 32 has a guide wire lumen 33 into which a guide wire can be inserted. Accordingly, the medical device 10 is a rapid exchange device in which the guide wire lumen 33 is formed only at the distal end part.

The materials of the outer tubular body 31 and the distal tube 32 are not particularly limited, and examples of the materials that can be preferably used include stainless steel, a shape memory alloy such as a nickel-titanium alloy, titanium, an alloy (silver wax component) made of silver, copper, zinc, or the like, an alloy (solder component) made of gold, tin, or the like, hard metal such as tungsten carbide, a polyolefin such as polyethylene or polypropylene, polyamide, polyester such as polyethylene terephthalate, various elastomers, a fluorine-based polymer such as ETFE, PEEK, polyimide, and polyacetal. In addition, the outer tubular body 31 may include a plurality of materials, and may have a reinforcing member such as a wire embedded therein.

The cutter 40 is a member for cutting and reducing the size of an object such as thrombus, plaque, and calcified lesion. Therefore, the term "cut" represents the action of applying a force to an object in contact with the cutter 40 and reducing the size of the object. A method for applying a force during cutting and the shape or type of the cut object are not limited. The cutter 40 is strong enough to cut the above-mentioned object. The cutter 40 is fixed to the distal end part of the drive shaft 20. The cutter 40 is a cylinder protruding further to the distal side with respect to the drive shaft 20. That is, the cutter 40 extends distally beyond the distal end of the drive shaft 20. The cutter 40 has a distal end provided with a sharp blade 41. A plurality of blades 41 is provided like the teeth on a saw blade, and are arranged side by side in the circumferential direction at the distal end of the cutter 40. The blade 41 is not particularly limited in shape. The blade 41 may not have a sawtooth shape, and may be, for example, a cylindrical blade formed substantially uniformly over the entire circumference. The cutter 40 may have a large number of fine abrasive grains instead of the blade 41.

Figure 5:
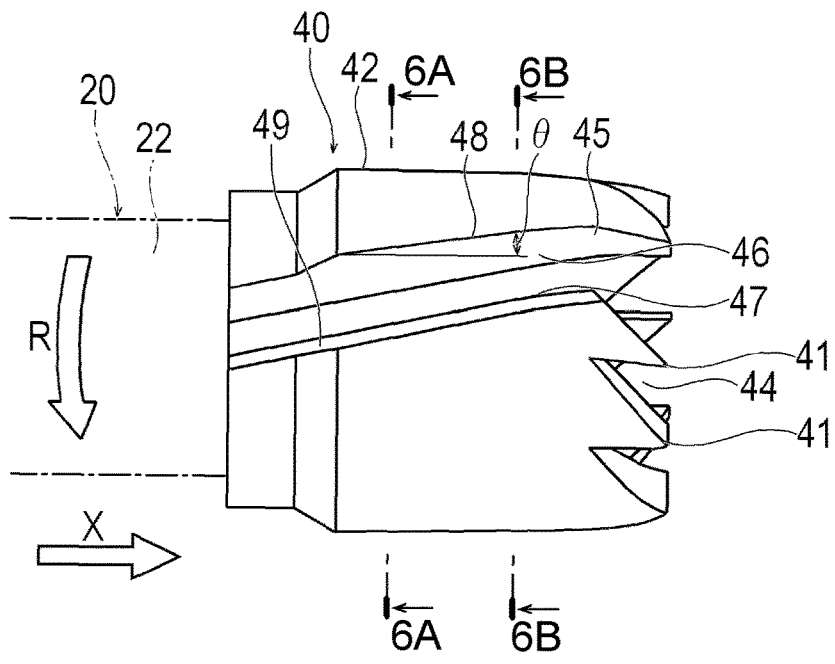
FIG. 5 is a front view of a cutter.
Figure 6A:
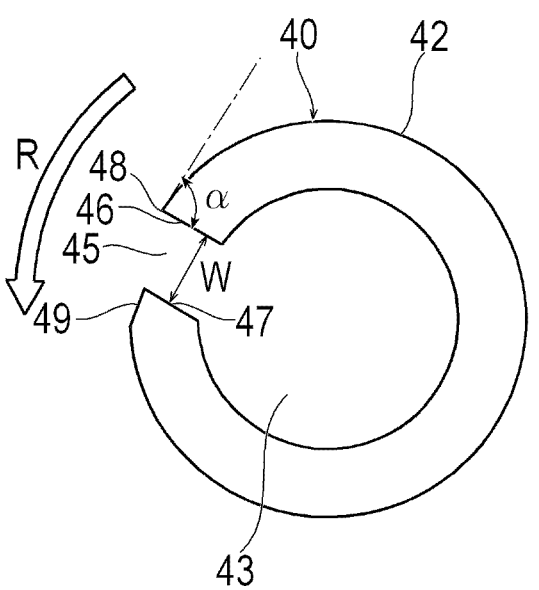
Figure 6B:
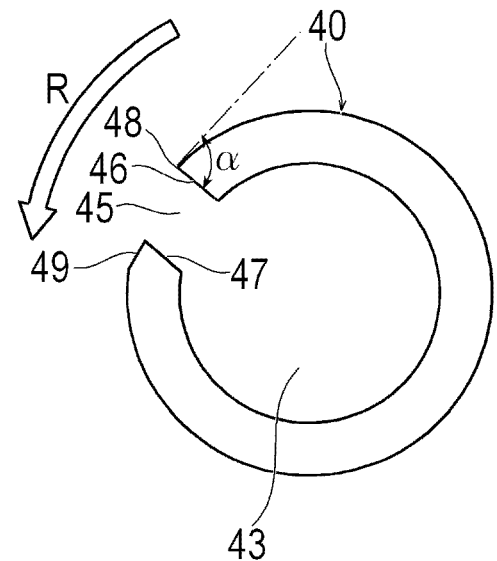
Figure 7:
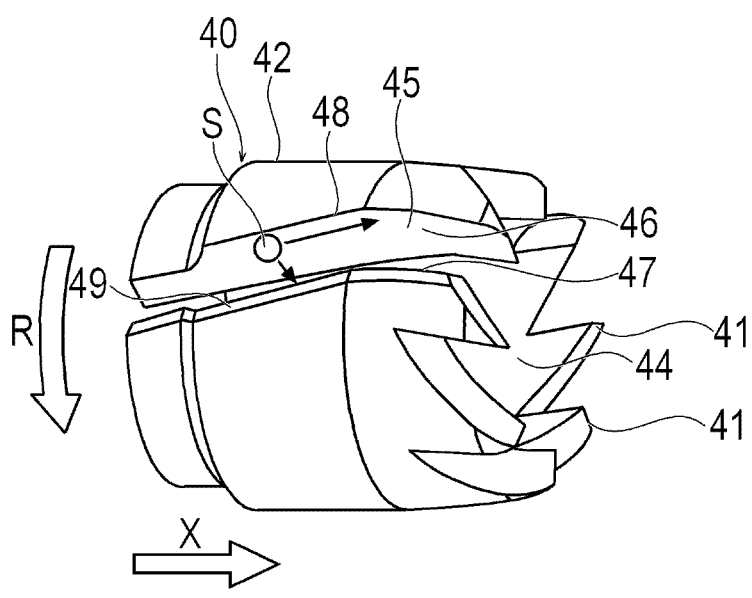
FIG. 7 is a perspective view of the cutter.

As illustrated in FIGS. 5 to 7, the cutter 40 includes a large-diameter portion 42 having an outer diameter larger than the outer diameter of portions of the cutter 40 on the distal side and on the proximal side at a substantially central portion in the axial direction which is the direction along the rotation axis. It is preferable that the outer diameter of the cutter 40 changes gradually, not stepwise, in the axial direction. A rotation direction R of the cutter 40 when the cutter 40 cuts the object is specified in one direction. The cutter 40 is fixed to the drive shaft 20 on the proximal side and has a lumen 43 communicating with the fluid lumen 22 of the drive shaft 20. The cutter 40 has, at the distal end, a distal end opening 44 where the lumen 43 is opened. The cutter 40 is formed with a guide portion 45 extending obliquely in a direction opposite to the rotation direction R in a distal direction X on the outer peripheral surface. The guide portion 45 is a slit penetrating from the outer peripheral surface to the inner peripheral surface of the cutter 40. The slit is also an opening where the lumen 43 of the cutter 40 opens to the outside. In the present embodiment, the guide portion 45 is formed entirely in the cutter 40 from the distal end of the cutter 40 to the proximal end of the cutter 40 in the axial direction, and communicates with the distal end opening 44. The distal end of the guide portion 45 is located between two blades 41 (cutting elements) arranged adjacent to each other in the circumferential direction at the distal end of the cutter 40. A guide portion inclination angle θ, which is an angle of inclination of the guide portion 45 extending along the outer peripheral surface of the cutter 40 with respect to the axial direction, exceeds 0 degrees but is less than 90 degrees, preferably 10 degrees to 70 degrees, and more preferably 30 degrees to 50 degrees. Thus, as shown in FIG. 5, for example, the central axis of the guide portion 45 is oriented other than parallel to the central axis or axial direction of the cutter. The guide portion 45 includes a guide surface 46 on the side in the direction opposite to the rotation direction R and a facing surface 47 on the side in the rotation direction R. When the cutter 40 rotates, the guide surface 46 comes into contact with the cut debris S or a liquid containing the cut debris S and applies a force to the cut debris S to guide the cut debris S in the distal direction. The facing surface 47 is a surface facing the guide surface 46. A width W (distance between the guide surface 46 and the facing surface 47) on the outer peripheral surface of the guide portion 45 may be constant at any position in the axial direction of the drive shaft 20, but may vary depending on positions in the axial direction.

A sharp second blade 48 (cutting element) capable of cutting the object is formed at an edge of the boundary between the guide surface 46 and the outer peripheral surface of the cutter 40. A guide surface inclination angle α, which is an angle of inclination of the guide surface 46 with respect to the outer peripheral surface of the cutter 40, may be less than 90 degrees, 90 degrees, or more than 90 degrees. When the guide surface inclination angle α is less than 90 degrees, the cutting effect by the second blade 48 is improved, and it is possible to effectively guide the cut debris S from the gap between the guide surface 46 and the facing surface 47 to the lumen 43 by applying a force to the inside of the cutter 40 in the radial direction to the cut debris S or the liquid in contact with the guide surface 46. When the guide surface inclination angle α is equal to or greater than 90 degrees or exceeds 90 degrees, the cutting effect by the second blade 48 is reduced, so that damage to a contacting living tissue such as a blood vessel is suppressed, and thus, safety is improved.

A chamfered portion 49 is formed at an edge of the boundary between the facing surface 47 and the outer peripheral surface of the cutter 40. The chamfered portion 49 may have, for example, a flat surface or a curved surface. When the chamfered portion 49 is formed on the facing surface 47, an object to be contacted easily enters the gap between the facing surface 47 and the guide surface 46, so that the second blade 48 formed on the guide surface 46 easily comes into contact with the object. Therefore, the object can be effectively cut by the second blade 48. The chamfered portion 49 may not be provided. In addition, when the chamfered portion 49 has a curved surface, it is possible to suppress scraping of the inner surface of a guiding catheter that movably houses the medical device 10, a blood vessel, or a lesion when the medical device 10 is moved to the vicinity of the lesion.

Figure 8A:
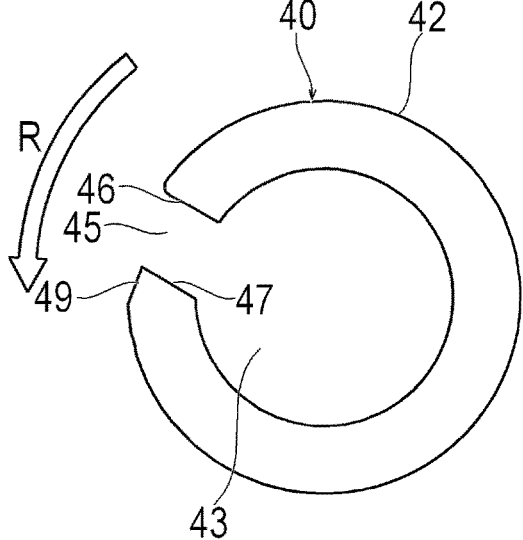

Further, the sharp second blade 48 may not be formed at the edge of the boundary between the guide surface 46 and the outer peripheral surface of the cutter 40 as in a first modification illustrated in FIG. 8A. That is, the cutter 40 may not include a cutting element other than the blade 41 at the distal end. Alternatively, the second blade 48 may be formed only in a part of the guide portion 45 in the axial direction. For example, the second blade 48 may not be formed at the edge of the boundary between the facing surface 47 and the outer peripheral surface of the cutter 40 in the large-diameter portion 42, and the second blade 48 may be formed at the edge of the boundary between the facing surface 47 and the outer peripheral surface of the cutter 40 on a side distal to and/or proximal to the large-diameter portion 42.

Figure 8B:
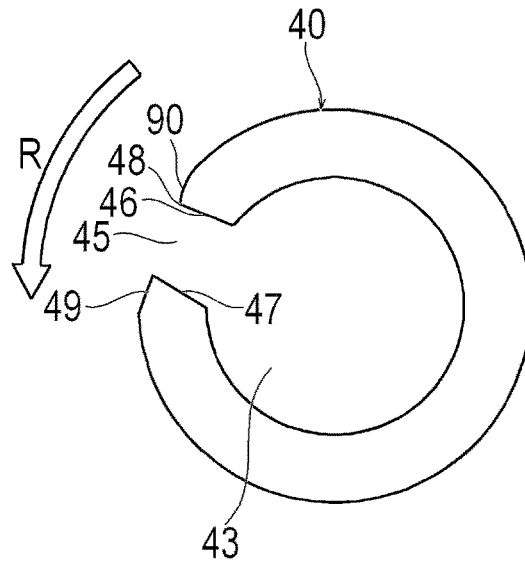

In addition, the cutter 40 may have the second blade 48 (cutting element) formed inside from the outer peripheral surface having a constant outer diameter in the radial direction in a cross section orthogonal to the rotation axis, as in a second modification illustrated in FIG. 8B. A buffer surface 90 that is adjacent to the second blade 48 and extends to the inside from the outer peripheral surface having a constant outer diameter in the radial direction is formed on the outside of the second blade 48 in the radial direction. The buffer surface 90 may have, for example, a smooth convex curved surface, or may have a smooth flat surface. The buffer surface 90 may be coated with a material having lower friction than peripheral members. Due to the formation of the buffer surface 90, the second blade 48 is less likely to come into contact with the living tissue. Therefore, it is possible to effectively cut a cutting target by the second blade 48 while preventing the damage of the living tissue by the second blade 48 to suppress the occurrence of blood vessel perforation and the like.

In addition, the cutting element disposed on the guide portion 45 of the cutter 40 may be, for example, a large number of fine abrasive grains instead of the sharp second blade 48. The abrasive grains may be provided at a position other than the guide portion 45. The guide portion 45 may have abrasive grains in addition to the second blade 48.

Figure 9A:
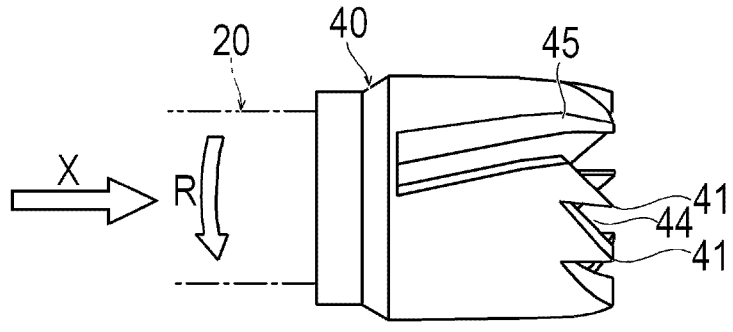
Figure 9B:
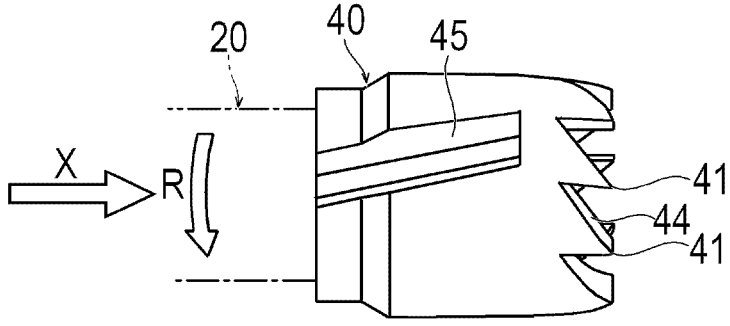
Figure 9C:
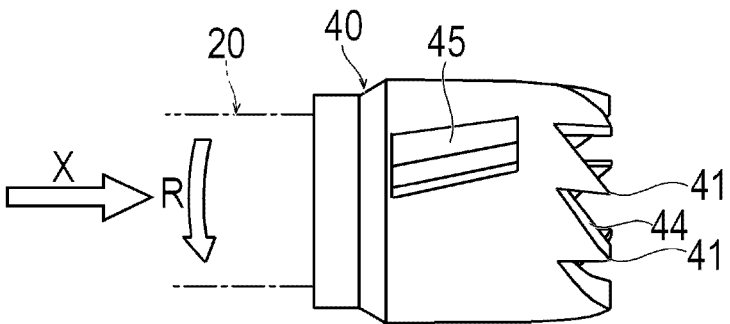

The guide portion 45 may be formed only in a part of the cutter 40 in the axial direction. That is, the guide portion 45 may be formed in a region from the distal end of the cutter 40 to a predetermined position on the proximal side as in a third modification illustrated in FIG. 9A. Alternatively, the guide portion 45 may be formed in a region from the proximal end of the cutter 40 to a predetermined position on the distal side as in a fourth modification illustrated in FIG. 9B. Alternatively, the guide portion 45 may be formed in a region from a position proximal to the distal end of the cutter 40 to a position distal to the proximal end of the cutter 40 as in a fifth modification illustrated in FIG. 9C.

Figure 10:
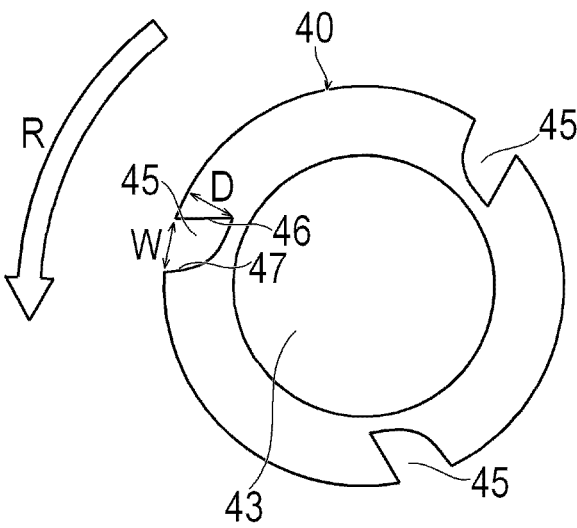
FIG. 10 is a cross-sectional view illustrating a sixth modification of the cutter.
Figure 11:
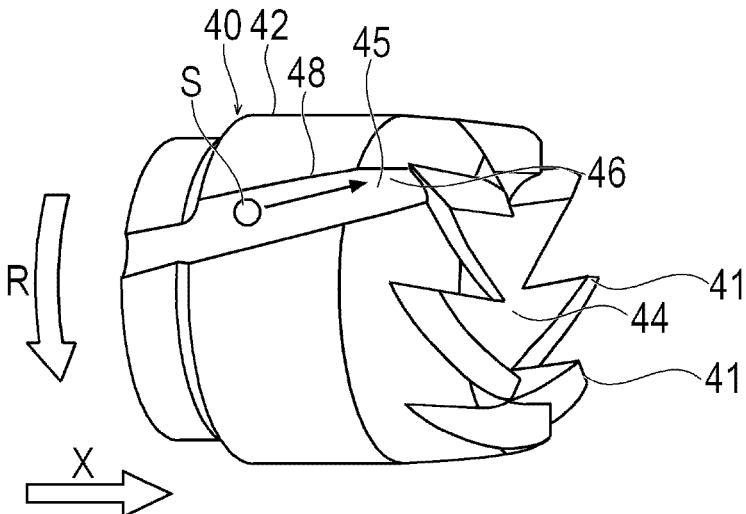
FIG. 11 is a perspective view illustrating the sixth modification of the cutter.

Further, the guide portion 45 of the cutter 40 may be formed in the outer peripheral surface as a groove as in a sixth modification illustrated in FIGS. 10 and 11. The cutter 40 has three guide portions 45 having a rotationally symmetric structure evenly arranged in the circumferential direction, but the number of guide portions 45 may be one, two, or four or more. The guide portion 45 does not penetrate from the outer peripheral surface to the inner peripheral surface. In this case, the cut debris S receiving a force from the guide surface 46 of the rotating cutter 40 is not directly guided to the lumen 43 toward the inside in the radial direction, but is guided to the distal end opening 44 on the distal side. A depth D of the guide portion 45 having a groove shape from the outer peripheral surface may be constant at any position in the axial direction, but may vary depending on positions in the axial direction. For example, the depth D of the guide portion 45 is preferably deeper on the distal side than on the proximal side. In the guide portion 45, the distal direction X is a direction in which the cut debris S is conveyed. Therefore, a flow path on the side in the distal direction X, which is a direction in which the cut debris S is conveyed, can be increased in the guide portion 45, so that the cut debris S can be effectively conveyed to the distal side.

In addition, the width W (distance between the guide surface 46 and the facing surface 47 on the outer peripheral surface) of the guide portion 45 having a groove shape (or a slit shape) may be constant at any position in the axial direction, but may vary depending on positions in the axial direction. For example, the width W of the guide portion 45 may be greater on the distal side than on the proximal side. When the width W of the guide portion 45 on the distal side is increased, a flow path on the side in the distal direction X, which is a direction in which the cut debris S is conveyed, can be increased in the guide portion 45, so that the cut debris S can be effectively conveyed to the distal side.

Figure 12:
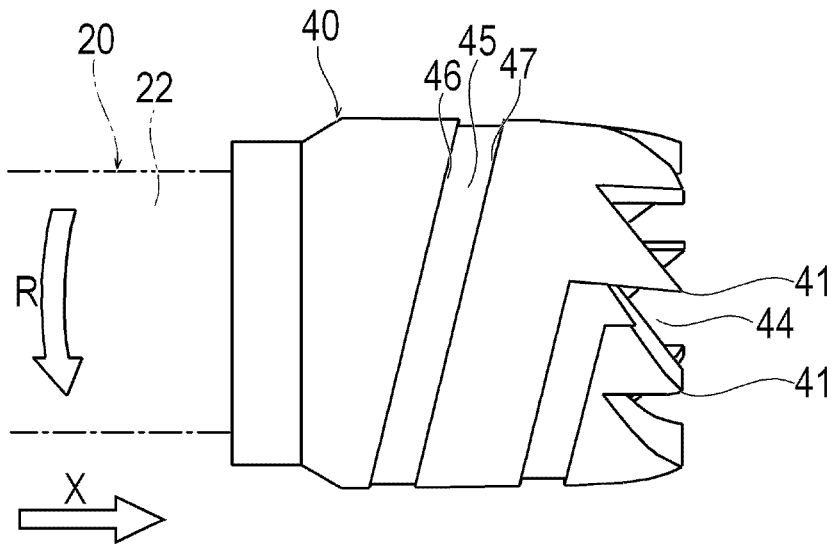
FIG. 12 is a front view illustrating a seventh modification of the cutter.

In addition, the guide portion 45 having a groove shape (or a slit shape) of the cutter 40 may be helically formed in the outer peripheral surface of the cutter 40 over 360 degrees as in a seventh modification illustrated in FIG. 12.

Figure 13:
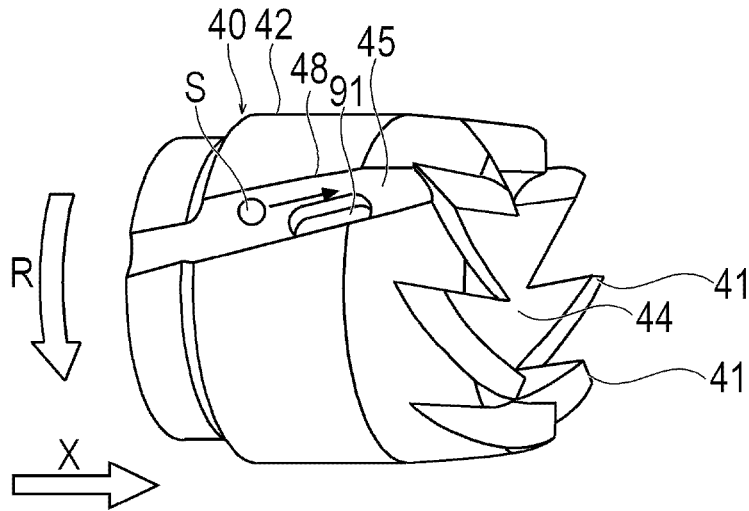
FIG. 13 is a perspective view illustrating an eighth modification of the cutter.

In addition, the guide portion 45 of the cutter 40 may include a groove and an opening 91 (or slit) penetrating the inner peripheral surface in the middle of the groove as in an eighth modification illustrated in FIG. 13. With this configuration, the medical device 10 can also directly guide and collect the cut debris S to the lumen 43 of the cutter 40 from the opening 91, in addition to guiding the cut debris S to the distal side toward the distal end opening 44 by the guide portion 45.

Figure 14:
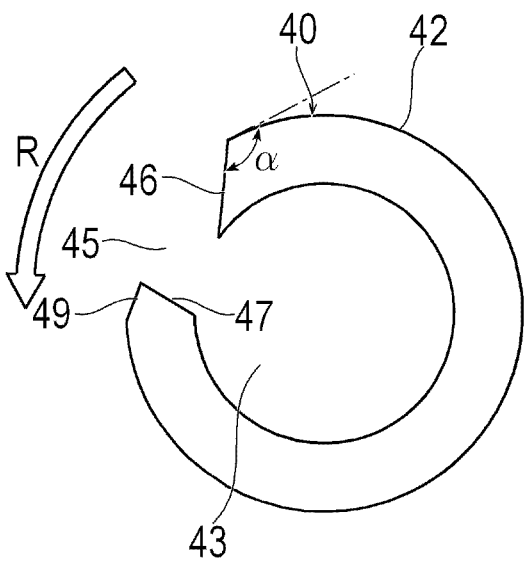
FIG. 14 is a cross-sectional view illustrating a ninth modification of the cutter.

In addition, the guide surface 46 may be formed to face outward in the radial direction as in a ninth modification illustrated in FIG. 14. That is, the guide surface inclination angle α, which is an angle of inclination of the guide surface 46 with respect to the outer peripheral surface of the cutter 40, may be more than 90 degrees but less than 180 degrees. This configuration can lower the cutting performance by the second blade 48, and thus, can prevent an occurrence of blood vessel perforation and the like by preventing damage on the living tissue by the second blade 48.

The material of the cutter 40 preferably has strength capable of cutting thrombus, and examples of the material preferably used include stainless steel, a shape memory alloy such as titanium, diamond, ceramics, or a nickel-titanium alloy, hard metal such as tungsten carbide, an alloy (silver wax component) made of silver, copper, zinc, or the like, and high speed steel. A resin including engineering plastic such as polyetheretherketone (PEEK) or polyacetal may be used as the material of the cutter 40.

Figure 3:
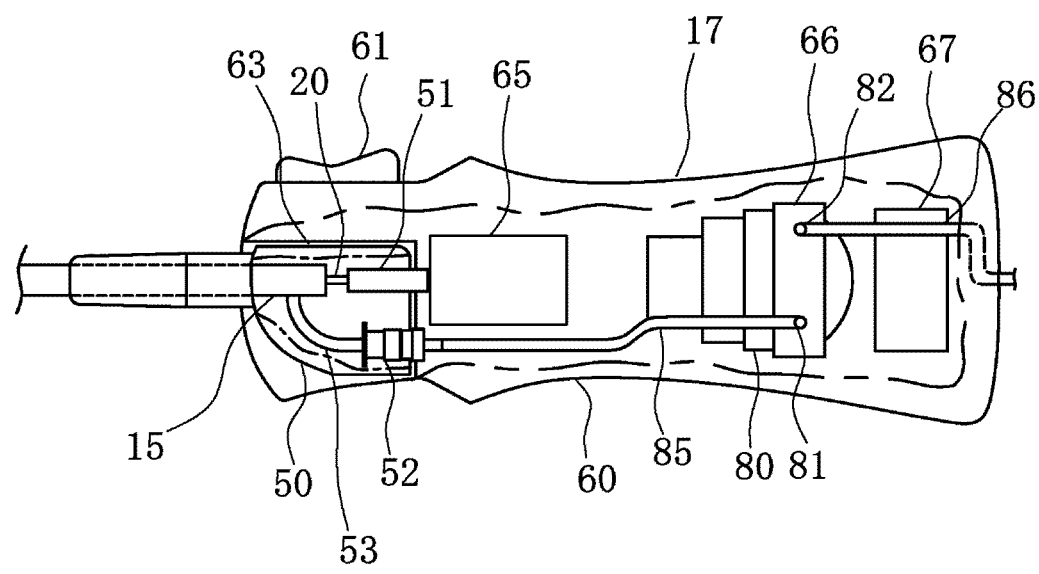
FIG. 3 is an enlarged front view of an area near a proximal end part of the medical device, and illustrates an internal structure of a handle.

The handle 17 will now be described. As illustrated in FIG. 3, the handle 17 includes a housing 60, and an operation switch 61 operated by an operator is provided on the distal side of the housing 60. A rotary drive source 65 which is a motor, a fluid drive source 66 which is a pump, and a power supply unit 67 which is a battery are housed in the housing 60. The rotary drive source 65 rotationally drives the drive shaft 20. The fluid drive source 66 moves the fluid from the distal side to the proximal side of the fluid lumen 22. That is, operation of the fluid drive source 66 moves conveys fluid from the distal end of the fluid lumen 22 to the proximal end of the fluid lumen 22. The power supply unit 67 is connected to the rotary drive source 65 and the fluid drive source 66 to supply power thereto.

The housing 60 has a hollow storage portion 63 on the distal side. A connection portion 50 of the shaft portion provided at the proximal end part of the shaft portion 15 is housed in the storage portion 63. The connection portion 50 of the shaft portion 15 includes therein a rotary connection portion 51 of the shaft portion 15 and a fluid connection portion 52 of the shaft portion 15. Therefore, positions of the rotary connection portion 51 of the shaft portion 15 and the fluid connection portion 52 of the shaft portion 15 are fixed to each other.

The shaft portion 15 branches inside the connection portion 50 of the shaft portion 15. The drive shaft 20 included in the shaft portion 15 is coupled to the rotary connection portion 51 of the shaft portion 15, the rotary connection portion 51 having a central axis coaxial with the drive shaft 20. The fluid lumen 22 is drawn from the shaft portion 15 to a branch tube 53, and the fluid connection portion 52 of the shaft portion 15 is provided at the distal end part of the branch tube 53.

Figure 4:
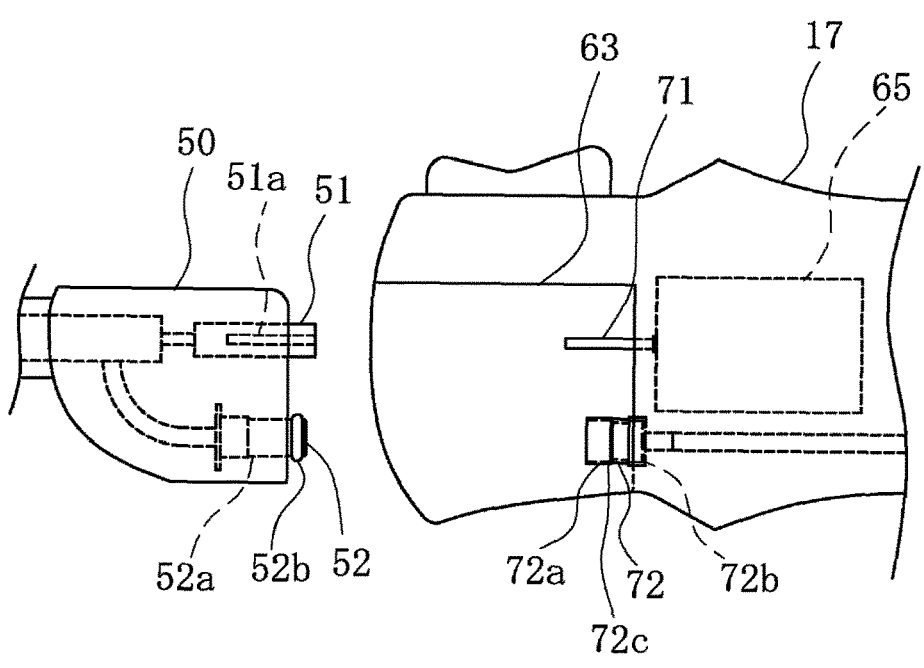
FIG. 4 is an enlarged exploded front view of the handle and a connection portion of a shaft portion.

As illustrated in FIG. 4, the rotary connection portion 51 of the shaft portion 15 has a shaft insertion portion 51a that opens to the proximal side. The rotary drive source 65 included in the handle 17 includes a rotary connection portion 71 of the handle 17 protruding to the storage portion 63. The rotary connection portion 71 of the handle 17 is a rotary shaft of the rotary drive source 65. The rotary connection portion 71 of the handle 17 is fixed to the housing 60 via the rotary drive source 65. When the rotary connection portion 71 of the handle 17 is inserted into the shaft insertion portion 51a of the rotary connection portion 51 of the shaft portion 15, the rotary connection portion 71 and the rotary connection portion 51 are connected to each other. The rotary connection portion 51 of the shaft portion 15 and the rotary connection portion 71 of the handle 17 are fixed to each other so as to be immovable in the radial direction and the circumferential direction, but are not fixed in the axial direction. That is, they are connected to each other without being locked to each other.

The fluid connection portion 52 of the shaft portion 15 has a tubular insertion portion 52a, and an O-ring 52b is attached to the distal end part of the tubular insertion portion 52a. The handle 17 is provided with a fluid connection portion 72 of the handle 17 to which the fluid connection portion 52 of the shaft portion 15 is connected. The fluid connection portion 72 of the handle 17 is fixed to the housing 60. The fluid connection portion 72 of the handle 17 has a connector 72a that receives the insertion portion 52a of the fluid connection portion 52 of the shaft portion 15. The connector 72a has a locking portion 72b that locks the fluid connection portion 52 of the shaft portion 15. The diameter of the inner surface of the connector 72a is slightly smaller on the distal side of the locking portion 72b. The O-ring 52b of the insertion portion 52a climbs over the small diameter portion and is elastically locked to the locking portion 72b. As a result, the fluid connection portion 52 of the shaft portion 15 is connected and locked to the fluid connection portion 72 of the handle 17.

The connection structure between the rotary connection portion 51 of the shaft portion 15 and the rotary connection portion 71 of the handle 17 is different from the connection structure between the fluid connection portion 52 of the shaft portion 15 and the fluid connection portion 72 of the handle 17. In addition, the rotary connection portion 51 of the shaft portion 15 and the rotary connection portion 71 of the handle 17 are connected to each other without being locked, whereas the fluid connection portion 52 of the shaft portion 15 and the fluid connection portion 72 of the handle 17 are connected and locked to each other. Therefore, if the lock on the suction side is released, the connection on the rotation side is also easily released. As a result, even in a case where suction cannot be performed during the treatment, it is possible to immediately stop the rotation and prevent an increase in the cut material in the blood vessel.

The connector 72a is formed of a resin material, and a front part and a rear part of the locking portion 72b in the axial direction serve as a deformable portion 72c that is elastically deformable in the radial direction. Therefore, when the operator pushes the deformable portion 72c so as to crush the deformable portion 72c in the radial direction with his/her finger, the deformable portion 72c is elastically deformed, and accordingly, the lock of the insertion portion 52a to the locking portion 72b is released. Thus, the fluid connection portion 52 of the shaft portion 15 can be easily detached from the connector 72a. On the other hand, if the operator does not intentionally deform the deformable portion 72c, the locked state of the insertion portion 52a with respect to the locking portion 72b is maintained, so that it is possible to prevent the fluid connection portion 52 of the shaft portion 15 from being unexpectedly or unintendedly detached from the fluid connection portion 72 of the handle 17.

The rotary connection portion 71 of the handle 17 and the fluid connection portion 72 of the handle 17 are both fixed to the housing 60 of the handle 17, and thus, their positions are fixed to each other. As described above, the positions of the rotary connection portion 51 of the shaft portion 15 and the fluid connection portion 52 of the shaft portion 15 are also fixed to each other. Therefore, the rotary connection portion 51 of the shaft portion 15 can be connected to the rotary connection portion 71 of the handle 17, and the fluid connection portion 52 of the shaft portion 15 can be connected to the fluid connection portion 72 of the handle 17 by housing the connection portion 50 of the shaft portion 15 in the storage portion 63 of the handle 17.

The fluid drive source 66 has an injection port 81 and a discharge port 82 in a pump body 80. An injection tube 85 extending from the fluid connection portion 72 of the handle 17 is connected to the injection port 81. A discharge tube 86 is connected to the discharge port 82. The discharge tube 86 is drawn out or extends out of the housing 60. A part or all of a section of the discharge tube 86 drawn out of (extending out of) the housing 60 is transparent or translucent. As a result, the operator can visually recognize the inside of the discharge tube 86. The section of the discharge tube 86 disposed inside the housing 60 may not be transparent or translucent. The discharge tube 86 is connected to a collection bag (not illustrated) outside the handle 17.

Next, a method of using the medical device 10 according to the present embodiment will be described using, as an example, a case where a lesion (object) such as a thrombus or a calcified lesion in a blood vessel is destroyed and sucked.

First, the operator inserts a guide wire (not illustrated) into the blood vessel and moves the guide wire to the vicinity of the lesion. Next, the operator inserts the proximal end of the guide wire into the guide wire lumen 33 of the medical device 10 illustrated in FIG. 3. Thereafter, the operator brings the medical device 10 to the vicinity of the lesion using the guide wire as a guide.

Next, the operator connects the rotary connection portion 71 of the handle 17 to the rotary connection portion 51 of the shaft portion 15 as illustrated in FIGS. 3 and 4. Then, the operator connects the fluid connection portion 72 of the handle 17 to the fluid connection portion 52 of the shaft portion 15. Thereafter, the operator actuates the rotary drive source 65 and the fluid drive source 66 of the handle 17. Thus, rotation of the rotary connection portion 71 and suction of the fluid connection portion 72 are started. The rotary connection portion 71 of the handle 17 rotates the drive shaft 20 via the rotary connection portion 51 of the shaft portion 15. As a result, the cutter 40 fixed to the distal end part of the drive shaft 20 rotates. The rotating cutter 40 cuts the lesion in the blood vessel.

The lesion cut by the blade 41 of the cutter 40 is turned into the cut debris S and moves to the proximal side through the lumen 43 of the cutter 40 along with liquid (mainly blood). The cut debris S is sucked into the fluid lumen 22 through the inlet port 26 of the drive shaft 20.

A portion of the cut debris S may not enter the lumen 43 through the distal end opening 44 of the cutter 40 and may flow to the proximal side on the outside of the cutter 40. The guide portion 45 formed in the cutter 40 extends in the distal direction X while inclining in a direction opposite to the rotation direction R. Therefore, when the cutter 40 rotates, the guide surface 46 of the guide portion 45 can come into contact with the cut debris S moving outside the cutter 40 or the liquid containing the cut debris S and apply a force toward the distal side to the cut debris S. In addition, when the guide portion 45 has a slit shape, the medical device 10 can directly guide the cut debris S to the lumen 43 through the guide portion 45. When the guide surface inclination angle α, which is an angle of inclination of the guide surface 46 with respect to the outer peripheral surface of the cutter 40, is less than 90 degrees, the cutting effect by the second blade 48 is improved, and it is possible to effectively guide the cut debris S from the gap between the guide surface 46 and the facing surface 47 to the lumen by applying a force to the inside of the cutter 40 in the radial direction to the cut debris S or the liquid in contact with the guide surface 46. When the guide surface inclination angle α is equal to or greater than 90 degrees or exceeds 90 degrees, the cutting effect by the second blade 48 is reduced, so that damage to the living tissue such as a blood vessel is suppressed, and thus, safety is improved.

In a case where the cutting element such as the second blade 48 or abrasive grains is disposed in the guide portion 45, the guide portion 45 cuts a lesion such as thrombus and generates cut debris S. The guide portion 45 can effectively guide the cut debris S to the distal end opening 44 on the distal side and the lumen 43 on the inner side in the radial direction.

The lesion cut by the blade 41 or the second blade 48 of the cutter 40 is turned into the cut debris S and moves to the proximal side in the cutter 40 along with liquid (mainly blood). The cut debris S is sucked into the fluid lumen 22 through the inlet port 26 of the drive shaft 20.

The sucked cut debris S moves in the proximal direction through the fluid lumen 22, reaches the fluid connection portion 72 through the fluid connection portion 52, and then passes through the discharge tube 86 to be collected in a collection bag or the like outside the handle 17.

After the cutting of the lesion and the suction of the cut debris S are completed, the operator stops the operations of the rotary drive source 65 and the fluid drive source 66 of the handle 17. Thus, the cutting by the cutter 40 and the discharge of the cut debris S stop. Then, the medical device 10 is removed from the blood vessel, and the procedure is complete.

As described above, the medical device 10 according to the present embodiment includes: an elongated shaft portion 15 that includes a drive shaft 20 which is rotatable and a fluid lumen 22; and a cutter 40 that cuts an object, the cutter 40 being fixed to a distal end of the drive shaft 20 and including a lumen 43 communicating with the fluid lumen 22 and a distal end opening 44 communicating with the lumen 43, wherein the cutter 40 has at least one guide portion 45 that is a groove and/or a slit on an outer peripheral surface, and the guide portion 45 extends in a direction opposite to a rotation direction R in a distal direction X. With this configuration, when the cutter 40 rotates, the guide portion 45 applies a force to the distal side to a contacting object. Therefore, the medical device 10 can guide the cut debris S generated by cutting by the cutter 40 to the distal side where the distal end opening 44 is formed, and can effectively collect the cut debris S into the lumen 43 communicating with the fluid lumen 22.

At least a part of the guide portion 45 is a slit penetrating from the outer peripheral surface to the inner peripheral surface of the cutter 40. With this configuration, the medical device 10 can directly guide and collect the cut debris S to the lumen 43 of the cutter 40, in addition to guiding the cut debris S to the distal side by the guide portion 45.

At least a part of the guide portion 45 may be a groove formed in the outer peripheral surface of the cutter 40. With this configuration, the medical device 10 can limit the depth D of the guide portion 45, thereby being capable of cutting a cutting target that is a lesion while suppressing the occurrence of blood vessel perforation and the like by preventing damage of a contacting living tissue such as a blood vessel. In addition, the medical device 10 can limit a collection path for collecting the cut debris S into the lumen 43 of the cutter 40 communicating with the fluid lumen 22 to the distal end opening 44. Therefore, the medical device 10 can suppress excessive discharge of blood by the fluid lumen 22.

The depth D of the groove of the guide portion 45 may be deeper on the distal side than on the proximal side of the cutter 40. With this configuration, the medical device 10 can increase a flow path on the side in the distal direction, which is a direction in which the cut debris S is conveyed, in the guide portion 45, thereby being capable of effectively conveying the cut debris S to the distal side.

The width W of the guide portion 45 that is a length in a direction perpendicular to an extending direction of the guide portion 45 on the outer peripheral surface of the cutter 40 may be greater on a distal side than on a proximal side of the cutter 40. With this configuration, the medical device 10 can increase a flow path on the side in the distal direction X, which is a direction in which the cut debris S is conveyed, in the guide portion 45, thereby being capable of effectively conveying the cut debris S to the distal side.

The guide portion 45 has a cutting element for cutting an object. With this configuration, the medical device 10 can cut a cutting target by the guide portion 45 formed on the outer peripheral surface of the cutter 40, and thus, can directly guide the cut debris S generated in the guide portion 45 to the distal side in the guide portion 45 and effectively collect the cut debris S into the lumen 43, while effectively cutting the cutting target. In addition, the medical device 10 can cut the cutting target more widely as compared with a case of having only the blade 41 as the cutting element.

The cutting element of the guide portion 45 may be disposed on the guide portion 45 at a position different from a position of a large-diameter portion 42 having a maximum outer diameter of the cutter 40. With this configuration, the medical device 10 can effectively cut the cutting target while suppressing the occurrence of blood vessel perforation and the like by preventing damage of a contacting living tissue.

The cutting element of the guide portion 45 may be disposed radially inside a section having a maximum outer diameter in a cross section orthogonal to the rotation axis. With this configuration, the medical device 10 can effectively cut the cutting target while suppressing the occurrence of blood vessel perforation and the like by preventing damage of a contacting living tissue.

The cutter 40 has a plurality of blades 41 arranged so as to surround the distal end opening 44 at the distal end of the cutter 40, and the guide portion 45 communicates with the distal end opening 44 between two adjacent blades 41. With this configuration, the medical device 10 enables the cut debris S guided to the distal side by the guide portion 45 to effectively reach the distal end opening 44 through a gap that is easily ensured between the two blades 41.

The guide portion 45 has a guide surface 46. With this configuration, the medical device 10 can effectively apply a force to the cut debris S or a liquid containing the cut debris S by the guide surface 46 to thereby effectively guide the cut debris S in the distal direction.

The new medical device disclosed here is not limited to the above-described embodiment, and various modifications can be made by those skilled in the art within the technical idea of the disclosure here. For example, the type of the fluid drive source 66 is not limited to a pump that generates a negative pressure from the outside, and may be a pump such as a diaphragm pump in which the drive unit is in direct contact with the fluid.

The detailed description above describes embodiments of a medical device representing examples of the new medical device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents that fall within the scope of the claims are embraced by the claims.

What is claimed is:

1. A medical device that is operable to cut an object in a living body, the medical device comprising:

an elongated shaft portion that includes a drive shaft and a fluid lumen passing through the drive shaft and having an open distal end and an open proximal end, the drive shaft having a distal end, the drive shaft being a rotatable drive shaft that is rotatably driven in a rotational direction during operation of the medical device;

a cutter that cuts the object, the cutter being fixed to the distal end of the drive shaft and including a lumen that is in fluid communication with the fluid lumen in the drive shaft, the cutter including an open distal end that is in fluid communication with the lumen in the cutter, the cutter including an outer peripheral surface;

the cutter having at least one guide portion that is a groove and/or a slit on the outer peripheral surface of the cutter, the guide portion extending in a direction opposite the rotational direction in a distal direction;

the cutter including a plurality of blades arranged at the distal end of the cutter so that the plurality of blades surround the open distal end of the cutter; and the guide portion communicating with the open distal end of the cutter between two of the blades that are circumferentially adjacent to each other.

2. The medical device according to claim 1, wherein the cutter has an inner peripheral surface surrounding the lumen of the cutter, at least a part of the guide portion being a slit penetrating from the outer peripheral surface of the cutter to the inner peripheral surface of the cutter.

3. The medical device according to claim 1, wherein at least a part of the guide portion is a groove formed in the outer peripheral surface of the cutter, the groove extending through only a portion of a thickness of the cutter.

4. The medical device according to claim 3, wherein the groove of the guide portion includes a distal groove portion and a proximal groove portion, the distal groove portion being located distal of the proximal groove portion, a depth of the distal groove portion of the guide portion being deeper on than the proximal groove portion of the guide portion.

5. The medical device according to claim 1, wherein the guide portion has a width, the width of the guide portion being a dimension of the guide portion in a direction perpendicular to an extending direction of the guide portion on the outer peripheral surface of the cutter, the width of a distal portion of the guide portion being greater than the width of a proximal portion of the guide portion, the distal portion of the guide portion being distal of the proximal portion of the guide portion.

6. The medical device according to claim 1, wherein the guide portion includes a cutting element that cuts an object.

7. The medical device according to claim 6, wherein the cutter possesses an outer diameter, a portion of the cutter being a largest-diameter portion that has a largest outer diameter of the cutter, the cutting element being disposed on the guide portion at a position different from a position of the largest-diameter portion.

8. The medical device according to claim 6, wherein the cutting element is disposed radially inside a section of the cutter having a maximum outer diameter in a cross section orthogonal to a rotation axis of the cutter.

9. The medical device according to claim 1, wherein the guide portion has a guide surface.

10. A medical device positionable inside a lumen in a living body and operable to cut an object in the lumen, the medical device comprising:

an elongated drive shaft having a proximal end and an open distal end, the drive shaft including a fluid lumen that fluidly communicates with the open distal end of the drive shaft and that extends from the open distal end of the drive shaft toward the proximal end of the drive shaft, the drive shaft being a rotatable drive shaft that is rotatably driven in a rotational direction during operation of the medical device;

a cutter fixed to the distal end of the drive shaft so that the cutter rotates with the drive shaft about a rotational axis of the cutter, the cutter having a distal portion configured to cut the object, the cutter including a lumen that is in fluid communication with the fluid lumen in the drive shaft, the lumen in the cutter communicating with outside the cutter, the cutter including an outer peripheral surface;

the cutter including a groove and/or a slit that extends radially from the outer peripheral surface of the cutter toward the lumen in the cutter;

the cutter including a cutting element that extends along at least a portion of the groove and/or slit to cut the object when the cutter is rotated, the cutting element being located proximal of the distal portion of the cutter that is configured to cut the object; and the groove and/or slit being inclined at an angle greater than 0° and less than 70° relative to the rotational axis of the cutter as seen in a plan view so that the groove and/or slit extends from the proximal end of the groove and/or slit to the distal end of the groove and/or slit in a direction opposite the rotational direction.

11. The medical device according to claim 10, wherein the groove and/or slit has a length extending from the proximal end of the groove and/or slit to the distal end of the groove and/or slit, at least a portion of the length of the groove and/or slit passing through the cutter and communicating with the lumen in the cutter.

12. The medical device according to claim 10, wherein the groove and/or slit has a length extending from the proximal end of the groove and/or slit to the distal end of the groove and/or slit, the groove and/or slit passing through the cutter and communicating with the lumen in the cutter along an entirety of the length of the groove and/or slit.

13. The medical device according to claim 10, wherein the groove and/or slit is a groove that extends through only a portion of a thickness of the cutter so that the groove and the lumen in the cutter do not communicate with one another.

14. The medical device according to claim 10, wherein the distal end of the groove and/or slit terminates at a distal end of the cutter.

15. The medical device according to claim 14, wherein the distal portion of the cutter that is configured to cut the object includes a plurality of circumferentially arranged saw-teeth, the distal end of the groove and/or slit terminating at a location between circumferentially adjacent saw-teeth.

16. The medical device according to claim 10, wherein the groove and/or slit has a length extending from the proximal end of the groove and/or slit to the distal end of the groove and/or slit, the proximal end of the groove and/or slit being spaced distally from a proximal end of the cutter, the distal end of the groove and/or slit being spaced proximally from a distal end of the cutter.

17. A method comprising:

positioning a cutter in a lumen in a living body, the cutter being connected to a drive shaft, the cutter including a lumen that is in fluid communication with an open distal end of the cutter, the lumen in the cutter extending in a proximal direction from the open distal end of the cutter toward the drive shaft, the cutter including an outer peripheral surface, the outer peripheral surface of the cutter being provided with a groove and/or a slit extending in a first rotational direction in a distal direction;

moving the cutter to an object in the lumen in the living body; and rotating the cutter in a second rotational direction opposite the first rotational direction while the cutter is positioned adjacent the object so that the cutter cuts the object to produce debris.

18. The method according to claim 17, wherein at least a part of the groove and/or slit passes through the cutter and communicates with the lumen in the cutter, the method further comprising conveying the debris and fluid into the lumen in the cutter by way of the part of the groove and/or slit that passes through the cutter and communicates with the lumen in the cutter.

* * * * *